United States Patent [19]

Wozniak

[11] Patent Number: 4,622,970
[45] Date of Patent: Nov. 18, 1986

[54] VASCULAR EVERTING INSTRUMENT
[75] Inventor: John J. Wozniak, Columbia, Md.
[73] Assignee: The Johns Hopkins University, Baltimore, Md.
[21] Appl. No.: 770,492
[22] Filed: Aug. 29, 1985
[51] Int. Cl.[4] .................. A61B 17/08; A61B 17/04
[52] U.S. Cl. ........................................ 128/334 R
[58] Field of Search .............. 128/334 R, 334 C, 335; 604/271; 227/19; 29/447, 450

[56] References Cited

U.S. PATENT DOCUMENTS

| | | | |
|---|---|---|---|
| 2,086,371 | 8/1935 | Tear | 29/450 |
| 2,940,452 | 11/1958 | Smialowski | 128/334 R |
| 3,040,748 | 9/1959 | Klein et al. | 227/19 |
| 3,316,914 | 5/1967 | Collito | 128/334 C |
| 3,606,888 | 6/1969 | Wilkinson | 128/334 C |
| 3,908,662 | 9/1975 | Razgulov et al. | 128/334 C |
| 4,144,631 | 3/1979 | Fujio | 29/235 |
| 4,470,415 | 9/1984 | Wozniak | 128/334 C |

Primary Examiner—Richard C. Pinkham
Assistant Examiner—Garg Jackson
Attorney, Agent, or Firm—Robert E. Archibald; Carl I. Brundidge

[57] ABSTRACT

The invention concerns a means having two instruments for everting an end of a severed artery over a ferrule surrounding the artery. A handle of a flaring instrument is squeezed to rotate a head section. Arms mounted to the head section open in the manner of an iris-diaphragm mechanism to flare the arterial end. Another instrument, curved forceps, urge the artery via the ferrule into the head section such that the arterial end is everted over the ferrule. Two everted arterial ends may be joined by sutureless vascular anastomosis.

28 Claims, 14 Drawing Figures

VASCULAR EVERTING INSTRUMENT

STATEMENT OF GOVERNMENTAL INTEREST

The Government has rights in this invention pursuant to Contract No. N00024-85-C-5301 awarded by the Department of the Navy.

BACKGROUND OF THE INVENTION

The invention concerns a vascular everting tool for use in performing sutureless anastomosis.

Severed blood vessels and other tubular fluid carrying body members requiring anastomosis are frequently encountered in penetrating wounds inflicted during combat, civil violence and automobile accidents. Other surgical procedures requiring anastomosis are the bypassing of blocked tubular members or replacement of a portion of a vessel or other tubular member with a portion of a vessel taken from another part of the body. Still another surgical procedure requiring anastomosis is the replacement of a damaged or diseased vessel or other tubular member with a prosthesis. At the present time, when these types of surgical procedures are necessary and when the requisite skills and facilities are available, the tubular members are anastomosed using a suturing procedure. As can be appreciated, the suturing of blood vessels or other tubular members requires exquisite skill and is a time consuming procedure. Under combat or emergency conditions, the requisite skills, facilities and time may not be available to prevent loss of limb or life.

U.S. Pat. No. 2,940,452 to Smialowski teaches a vascular everter for everting the end of a blood vessel over the end of a bushing, or the like, preparatory to effecting the suturing operation. Smialowski discloses a tubular body having a diaphragm of rubber over one end, a bore of the tubular body being enlarged to form an annular recess. Within the bore is a plunger, which upon manual depression, causes distention of the diaphragm. As pressure on the plunger is progressively released, the body is slowly reciprocated until the bushing enters the annular recess. The instrument is withdrawn leaving the blood vessel end everted on the bushing. In a second embodiment, a lever is used to manipulate the plunger. It is apparent, however, that as the plunger is withdrawn or the body is worked forward, the diaphragm tends to return to its flattened state, allowing the artery end to close to its normal shape. Thus the eversion is prevented and the artery is merely jammed into the annular recess.

U.S. Pat. No. 3,040,748 to Klein et al., shows a vascular positioning method and device, generally similar to the Smialowski device. However, the Klein et al. device includes a suction air pump for drawing a blood vessel through a bushing. A cylinder is moved towards a bushing, which causes a collar to be turned inside out by engagement of an end edge with a flange of the collar. This action everts the overlying portion of the blood vessel. Obviously, the requirement of a pressure-creating device (the suction air pump) makes the Klein et al everter awkward to manipulate.

In U.S. Pat. No. 4,470,415 to Wozniak, an everting tool is disclosed having a head portion with rotatable and stationary sections. Wire arms are mounted to the rotatable section and are guided by staples attached to the stationary portion. Upon actuation of a shaft, a gear drives the rotating portion relative to the stationary portion, such that arms open to flare an artery end. Also included is a balloon mechanism, used to pull the artery through the flared end. In this design endothelial cell damage conceivably may occur due to the pressure and movement of the balloon within the vessel lumen. Blood flow over damaged endothelial cells of the vessel may cause clotting, restricting blood flow, and defeating the purpose of anastomosis. The device disclosed in the Wozniak patent is used in sutureless end-to-end anastomosis, to join artery ends, for example.

SUMMARY OF THE INVENTION

The invention relates to an apparatus having two instruments for everting blood vessel ends and the like having a range of lumen diameters, for sutureless anastomosis, the anastomosis technique being fully described in U.S. Pat. No. 4,470,415 to Wozniak.

The invention utilizes a first instrument comprising an iris-diaphragm mechanism to flare the leading edge of a lumen. An outer ring is fixed and contains six pivoting, wire expansion arms that terminate in short perpendicular segments. An inner ring contains six wire hoops through which the expansion arms pass. Rotation of the inner ring, in response to lever movement, causes the arms to expand or contract radially. A second instrument (curved forceps) is used to urge the vessel toward the flaring instrument. In use, a thin wall ferrule is placed on one portion of a transected artery, for example. The flaring expansion arms (fully closed) are then positioned within the lumen, and the everter handle squeezed, causing the iris-diaphragm mechanism to flare the leading edge of the lumen. A thumb-operated brake may be engaged to keep the expansion arms in any open position. The curved forceps are used to push the ferrule through the opened iris-diaphragm mechanism leaving the artery wall everted over the ferrule. The same sequence is performed on the other end of the artery. Any endothelial cells at the everted leading edge of the artery, which might have been damaged when contacted by the invention, are now external to the blood vessel. Thus, the blood's tendency to clot within the vessel is minimized, since the lumen of the anastomosed vessel comprises undamaged cells. The two ends of the transected artery are brought together and joined, as described in the Wozniak patent for example by means of a low temperature heat-shrinkable sleeve of polymeric material.

DETAILED DESCRIPTION OF THE INVENTION

Figure 1:
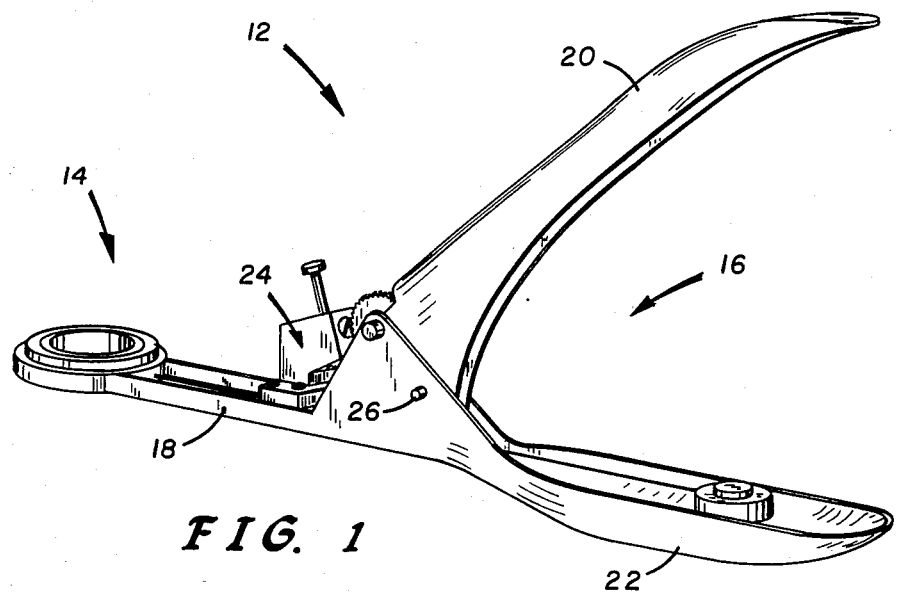
FIG. 1 shows a perspective view of a tool for flaring an end of a severed artery.

FIG. 1 shows the flaring instrument 12 in accordance with the present invention. The instrument 12 is comprised of a head portion 14 and a handle portion 16, connected via a channel 18. The head portion 14 engages a blood vessel or other tubular body member (not shown) to evert the vessel end, as described below. The handle portion 16 comprises a lever 20 and a grip 22 which are urged toward one another, or squeezed, by the surgeon, causing the head portion 14 to operate. Once the lever 20 has been squeezed toward the grip 22, a brake mechanism, generally shown at 24, may be employed to lock the handle portion 16. In this manner the surgeon need not maintain a forceful grasp about the handle portion 16 but may relax his hand muscles in order to accurately manipulate the flaring instrument 12. The details of the brake mechanism 24 are discussed with respect to FIG. 3. To protect the head portion 14 from damage during actuation, the motion of the handle portion 16 is limited by a stop 26 (see FIG. 3).

Figure 2:
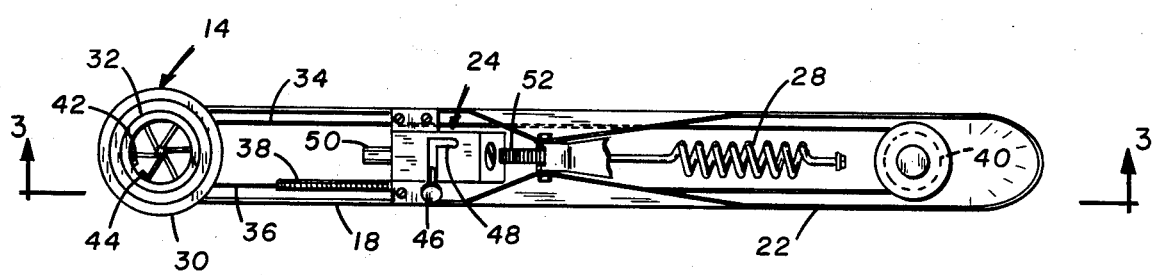
FIG. 2 reveals a top view of the FIG. 1 tool, with part of the handle cut away.
Figure 3:
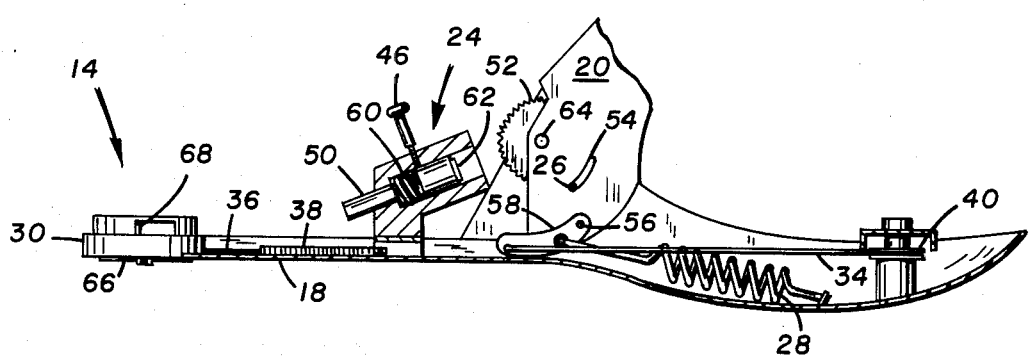
FIG. 3 is a sectional view taken at line 3—3 of FIG. 2.

FIG. 2 shows the flaring instrument 12 as viewed from the top. A biasing spring 28 is fastened to the grip 22 and is connected to the lever 20, urging the handle portion 16 to its return or open position. In FIG. 3 the specifics of the connection between the biasing spring and the lever 20 are evident. The head portion 14 of the flaring instrument 12 includes a stationary section 30 on which a rotatable section 32 is mounted to slide through a few degrees of rotation. The motion of the lever 20, when actuated, is transferred via a cable 34 which links the rotatable section over a pulley 40 to the lever 20. As the lever 20 is closed toward the grip, the tension of the cable 36 increases, moving the cable in a clockwise manner. Since the cable is affixed at 42, by means of braze for instance, to the rotatable section, the rotatable section will slide through a few degrees of clockwise rotation. A second, shorter cable 36 is affixed at 44 to the rotatable section, but owing to return spring 38, biases the rotatable section counter-clockwise to a return position, once the lever 20 is opened. The brake mechanism 24 includes a thumb-lever 46 which is moved in a locking-slot 48. When the surgeon has squeezed the handle portion 16 to appropriately spin the rotatable section, a simple flick of the thumb, of the hand grasping the flaring instrument 12, will lock the handle in place. Movement of the thumb-lever in the locking-slot permits a plunger 50 to slide right, as viewed in FIG. 2, and to engage a gear 52 that is connected to the lever 20.

FIG. 3 shows a cutaway view of the flaring instrument 12 10 as taken at line 3—3 of FIG. 2. Here, the actuation mechanism of the handle portion 16 is evident. Lever 20 has a curved slot 54 the lower end of which is shown engaging the stop 26. The downward movement of lever 20 is limited by the length of the curved slot 54, the lever being movable until the stop 26 is contacted by the upper end of the curved slot. The curved slot 54 and slot 26 prevent damage to the rotatable section 32. Pivotably pinned at 56 to the lever 20 is a connector arm 58. The biasing spring 28 is fastened to the connector arm 58, and is thereby connected to the lever 20. As the lever is squeezed, the connector arm 58 slides left along the channel 18, since the biasing spring 28 keeps the connector arm 58 from pivoting upward about pin 56. Upon release of the lever 20, the biasing spring 28 pulls the connector arm 58 right, causing the lever 20 to rise. The pivotally pinned connector arm 58, fastened to the biasing spring 28 as shown, insures that the cable 34 moves laterally only. Any up or down motion in the cable 34 might cause the cable 34 to slip from the pulley 40.

In FIG. 3, the details of the brake mechanism 24 are visible. The brake mechanism 24 is in its disengaging position, the thumb-lever 46 locking the plunger 50 left, against the compressed coils of a brake spring 60. Actuation of the thumb-lever 46 allows the brake spring 60 to expand, driving the plunger 50 right such that a shim 62 engages the teeth of the gear 52. The gear 52 is secured to the lever 20, to rotate as a unit about the gear's axle 64. The shim 62 prevents counter-clockwise rotation of the gear 52 as urged by the force of the biasing spring 28. At the head portion 14, arms 66 are illustrated in a cluster, or closed grouping, in response to the handle portion's 16 open position. The function of the arms 66 is discussed below. A turn-stop 68 limits the degrees through which the rotatable section 32 turns to protect the arms 66.

Figure 4:
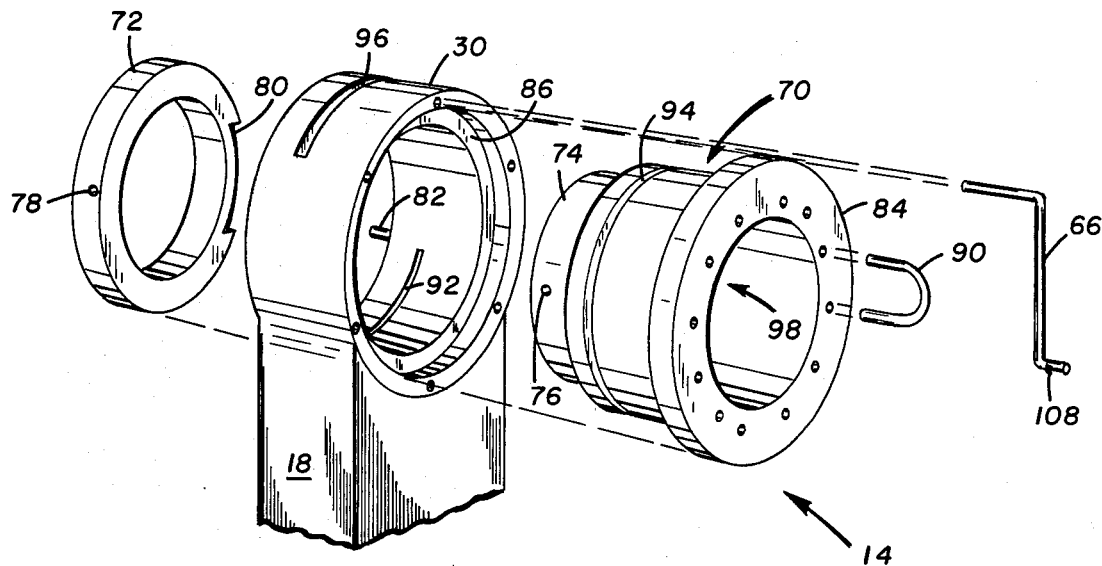
FIG. 4 portrays the head section of the FIG. 1 tool in an exploded view.

FIG. 4 portrays the head portion 14 in an exploded view. The rotatable section 14 includes a spool 70 and a locking collar 72 which is secured about the neck 74 of the spool 70 at holes 76, 78 (by a pin, for instance). A groove 80 in the locking collar with a rod 82 forms the turn-stop 68 of FIG. 3. The spool 70 is permitted to rotate until either end of the groove 80 meets the rod 82. The spool 70 has a flange 84 for flush mating with a recess 86 in the stationary section 30. Arms 66 and staples or hoops 90 are respectively mounted to the stationary section 30 and the spool 70. The arms 66 pivot freely in the stationary section 30, while the hoops 90 are sprung into the spool 70. Upon assembly of the head portion 14, the spool 70 is recessed in the stationary section 30 and the locking collar 72 is secured. The cable 34 is guided through the channel 18, through a lower radial slot 92 and around an annular groove 94 of the spool 70. The cable 34 initially exits the stationary section 30 via an upper radial slot 96, but is fed back into the upper radial slot 96, through a hole (not visible) into a bore 98 of the spool 70. Inside the bore 98, the cable 34 is affixed by means of braze, for instance, to the spool 70. With respect to the cable 36, a second hole is provided in the spool 70 for similar affixing of the cable 36, the holes being visible in FIG. 5. The arms 66 are slid into the stationary section 30, and the hoops 90 are sprung into the flange 84 over the arms 66. The end of each arm 66 is formed with an extension which is substantially perpendicular to the arm. Attached to the end of each extension is a barb 108, perpendicular to the arm 66 and located midway on the extension. The barb 108, during operation of the flaring instrument, impales the arterial wall to insure the artery does not slip when being flared or everted.

Figure 5:
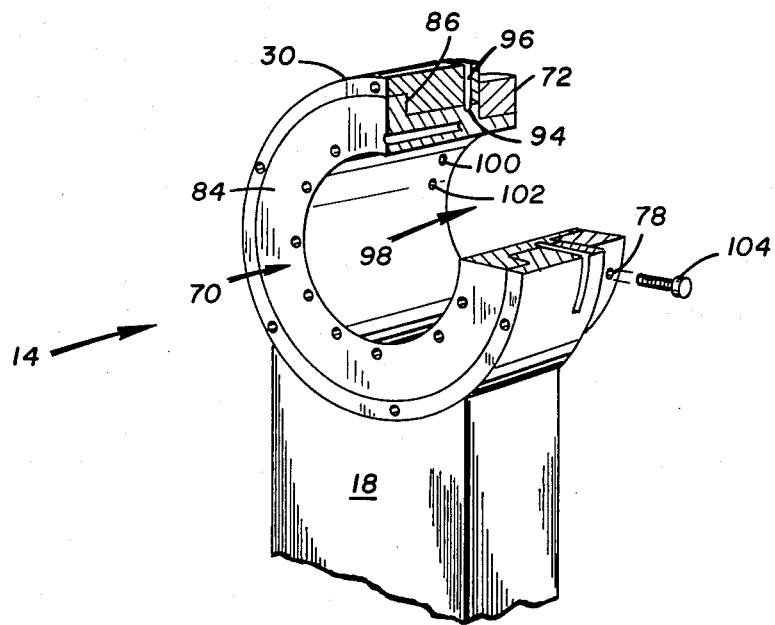
FIG. 5 displays a half section view of the head section, partially assembled.

FIG. 5 illustrates the head portion 14 as assembled, but in a sectional view, and is rotated ninety degrees clockwise relative to the FIG. 4 view. The flange 84 rests upon the recess 86 to be flush with the stationary section 30. The flange 84 slides along the recess 86 as the rotatable section 32 is rotated. The upper radial slot 96 is aligned with the annular groove 94 of the spool 70. Here the two holes 100, 102 are seen, through which the cables 34 and 36 are respectively threaded for affixing to the inside of the spool 70. A screw 104 secures the locking collar 72 to the spool 70 via hole 78.

Figure 6:
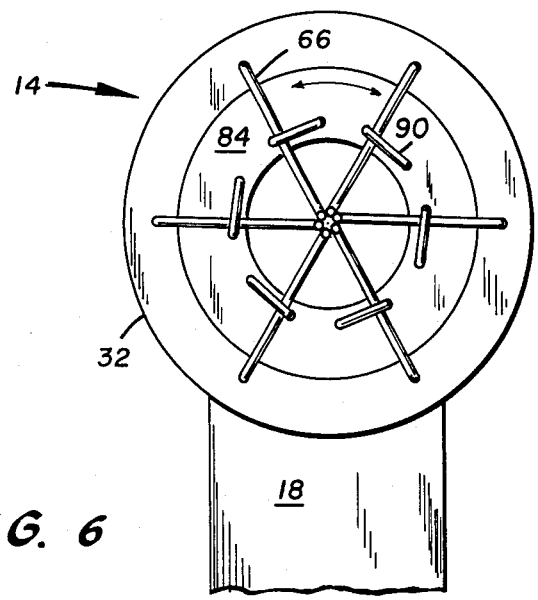
FIG. 6 shows the head section with the arms closed.
Figure 7:
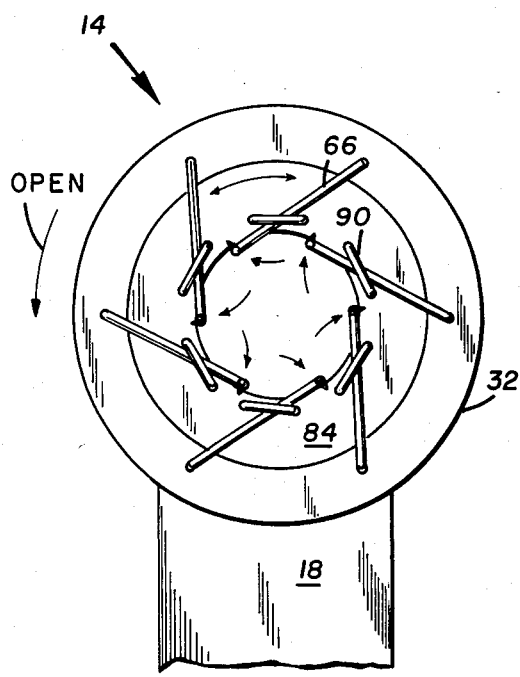
FIG. 7 shows the head section with the arms opened.
Figure 8:
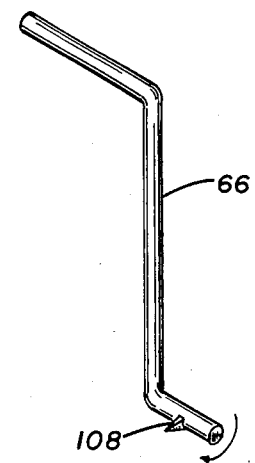
FIG. 8 details one arm.
Figure 9:
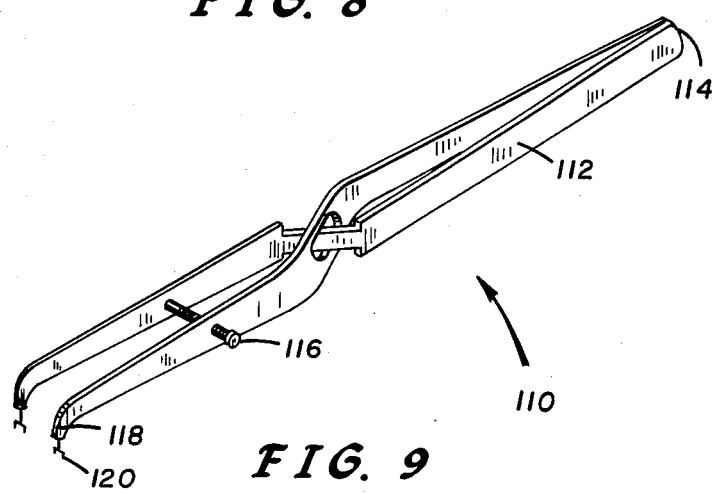
FIG. 9 features curved forceps for guiding the severed artery toward the FIG. 1 tool.
Figure 10A:
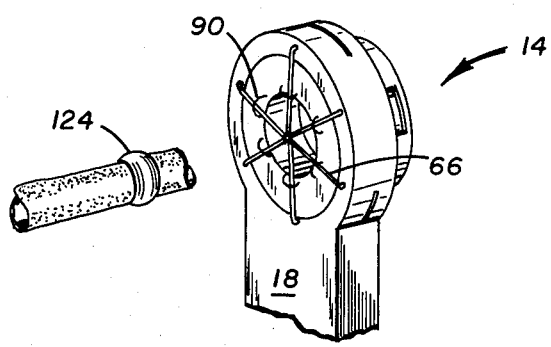
FIGS. 10a–e sequentially exhibits the use of the FIGS. 1 and 9 tools in everting an arterial end.
Figure 10B:
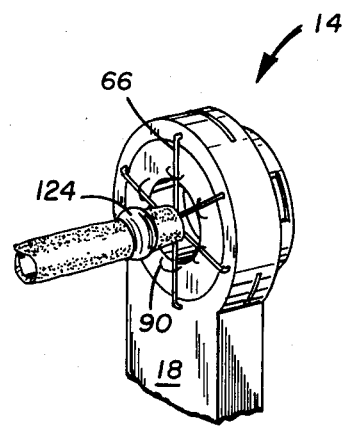
Figure 10C:
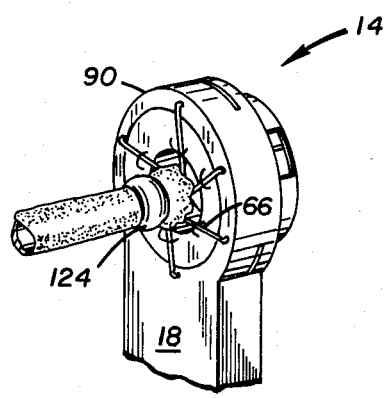
Figure 10D:
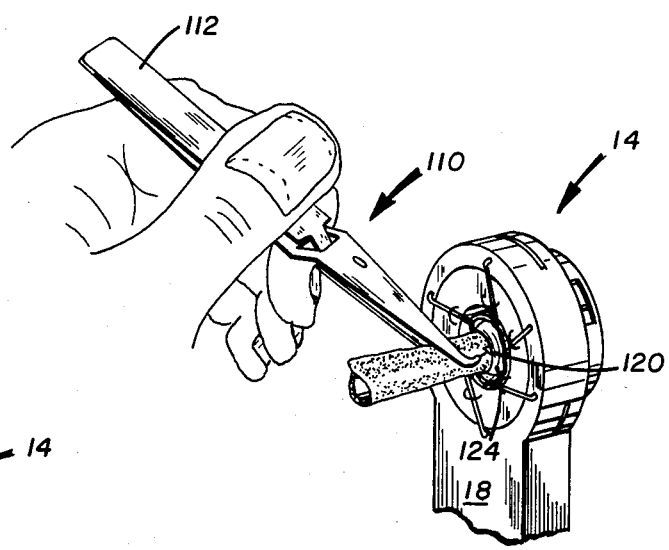
Figure 10E:
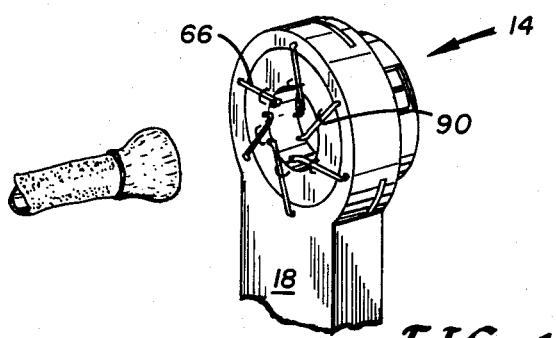

FIGS. 6 and 7 reveal the operation of the iris-diaphragm mechanism (the head portion), used to flare the